United States Patent
Marshall et al.

(10) Patent No.: US 9,808,581 B2
(45) Date of Patent: Nov. 7, 2017

(54) PLUNGER RETRACTION FOR LEAK PREVENTION IN INJECTION DEVICE

(71) Applicant: OWEN MUMFORD LIMITED, Woodstock (GB)

(72) Inventors: Jerry Marshall, Oxford (GB); Jakub Tomaszewski, Woodstock (GB)

(73) Assignee: OWEN MUMFORD LIMITED, Woodstock (GB)

( * ) Notice: Subject to any disclaimer, the term of this patent is extended or adjusted under 35 U.S.C. 154(b) by 0 days.

(21) Appl. No.: 14/910,389

(22) PCT Filed: Jul. 2, 2014

(86) PCT No.: PCT/GB2014/052007
§ 371 (c)(1),
(2) Date: Feb. 5, 2016

(87) PCT Pub. No.: WO2015/036729
PCT Pub. Date: Mar. 19, 2015

(65) Prior Publication Data
US 2016/0175536 A1 Jun. 23, 2016

(30) Foreign Application Priority Data

Sep. 10, 2013 (GB) .................................. 1316079.1

(51) Int. Cl.
*A61M 5/315* (2006.01)
*A61M 5/20* (2006.01)

(52) U.S. Cl.
CPC .......... *A61M 5/31566* (2013.01); *A61M 5/20* (2013.01); *A61M 5/31585* (2013.01);
(Continued)

(58) Field of Classification Search
CPC .......... A61M 5/31585; A61M 5/31553; A61M 5/20; A61M 5/31566
See application file for complete search history.

(56) References Cited

U.S. PATENT DOCUMENTS

| 5,114,406 A | 5/1992 | Gabriel et al. |
| 6,231,550 B1 | 5/2001 | Laughlin |

(Continued)

FOREIGN PATENT DOCUMENTS

| WO | 03/057285 A2 | 7/2003 |
| WO | 2007/063342 A1 | 6/2007 |
| WO | 2011/114122 A1 | 9/2011 |

OTHER PUBLICATIONS

International Search Report, dated Aug. 28, 2014, from corresponding PCT application.

(Continued)

*Primary Examiner* — Theodore Stigell
*Assistant Examiner* — Benjamin Koo
(74) *Attorney, Agent, or Firm* — Young & Thompson

(57) ABSTRACT

An injection device includes a housing, a plunger, a drive gear and a release trigger. The plunger includes a leadscrew and a cap attached thereto where, in use, the cap engages a bung of a cartridge containing medicament. The drive gear within the housing engages with the leadscrew such that rotation of the drive gear around the leadscrew drives the plunger axially through the housing towards the bung. The trigger includes a locking ring having generally axially extending teeth for engaging with corresponding teeth on the drive gear. The trigger is generally axially movable between an engaged position where the teeth are engaged and prevent rotation of the drive gear, and a disengaged position where the teeth are disengaged and enable rotation of the drive gear. Movement of the trigger between the disengaged and engaged position causes counter-rotation of the drive gear and retracts the plunger away from the bung.

5 Claims, 6 Drawing Sheets

(52) U.S. Cl.
CPC ....... *A61M 5/3156* (2013.01); *A61M 5/31511* (2013.01); *A61M 5/31513* (2013.01); *A61M 5/31515* (2013.01); *A61M 5/31535* (2013.01); *A61M 5/31553* (2013.01); *A61M 2005/2026* (2013.01)

(56) References Cited

U.S. PATENT DOCUMENTS

| | | | | |
|---|---|---|---|---|
| 8,152,766 | B2* | 4/2012 | Karlsson | A61M 5/20 604/133 |
| 2007/0129687 | A1* | 6/2007 | Marshall | A61M 5/20 604/207 |
| 2011/0224622 | A1* | 9/2011 | Karlsson | A61M 5/20 604/211 |
| 2012/0248152 | A1 | 10/2012 | Weill et al. | |

OTHER PUBLICATIONS

GB Search Report, dated Mar. 5, 2014, from corresponding GB application 1316079.1.

* cited by examiner

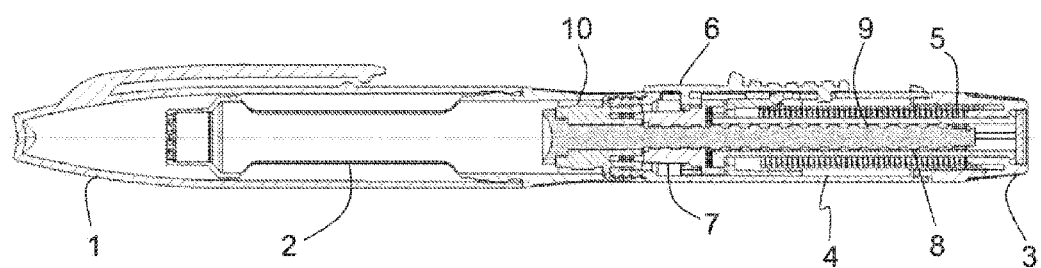
Figure 1 - Prior Art
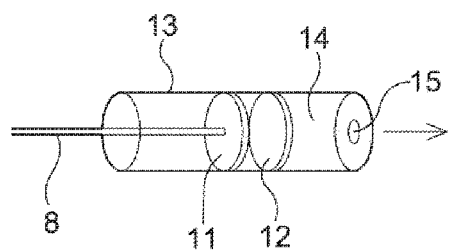
Figure 2 - Prior Art

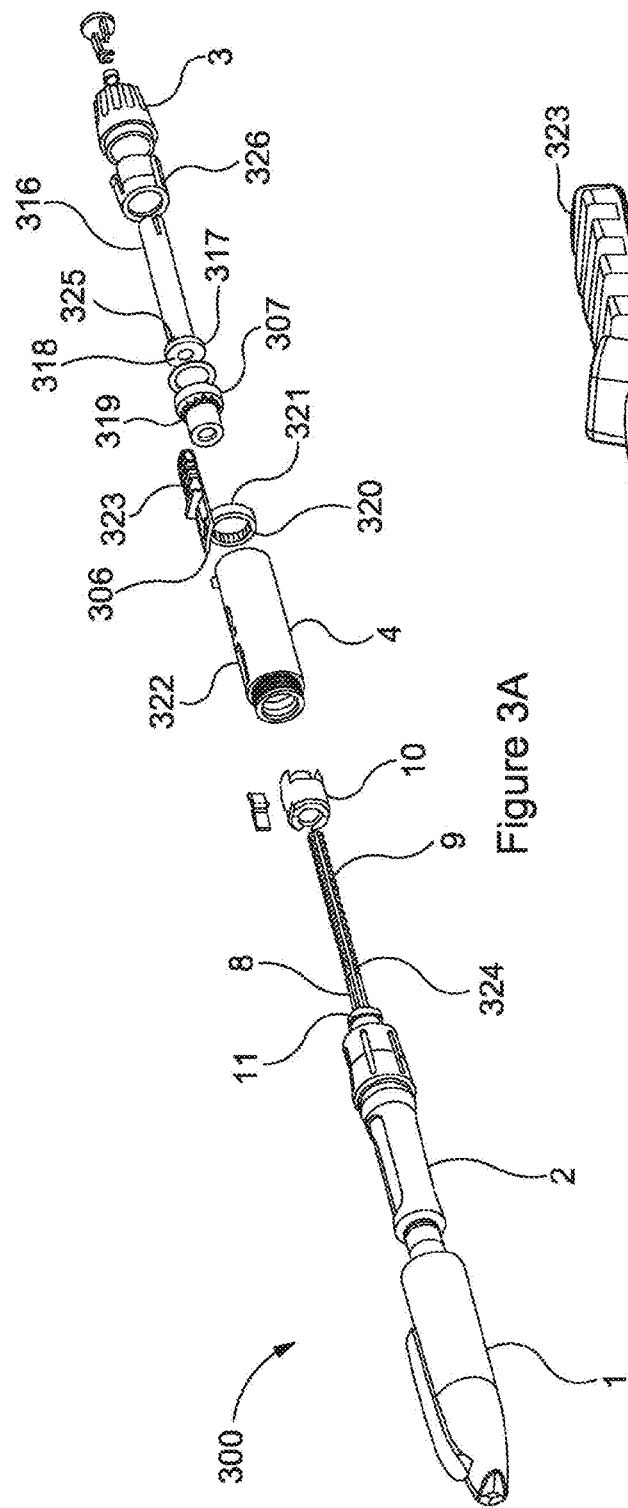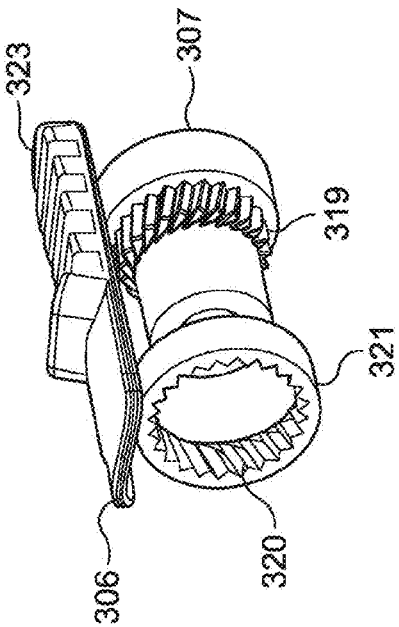

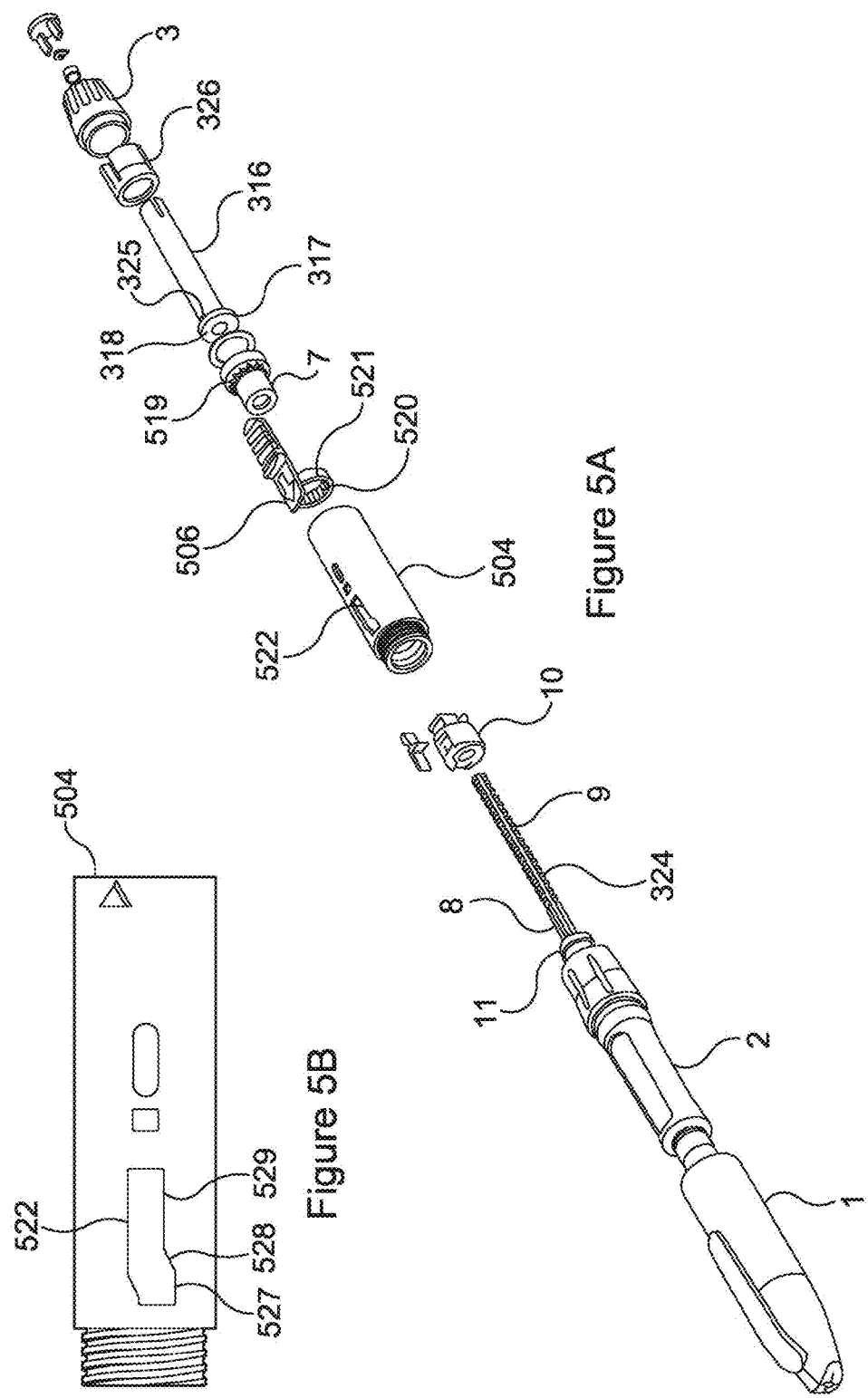

PLUNGER RETRACTION FOR LEAK PREVENTION IN INJECTION DEVICE

TECHNICAL FIELD

The present invention relates to an injection device, and to leak prevention in such invention devices.

BACKGROUND

WO2007063342 describes a generally pen-like syringe as shown in FIG. 1 and which is suitable for use with a cartridge containing a medicament. The cartridge is held within a cartridge housing and is adapted to receive a needle (not shown) which pierces a rubber septum sealing a proximal end (with respect to a user's skin) of the cartridge. A cap 1 is provided for covering the cartridge housing 2 and cartridge, and any attached needle. The syringe incorporates a dose metering device provided by a dose knob 3 which is rotatable with respect to the main housing 4 to a position related to the dose of medication to be injected. Rotation of the cap stores energy in a torsion spring 5, which is prevented from unwinding by cooperating splines. The user disengages the splines by means of a sliding trigger 6 coupled to the outside of the main housing 4, resulting in the unwinding of the spring. This in turn causes rotation of a drive gear 7 which is coupled to a plunger 8 via a quick pitch screw thread 9. During firing, the plunger is prevented from rotating by splines in a rewind knob 10 which is rotationally fixed relative to the main housing 4 when the cartridge housing 2 is attached to the main housing 4. The splines interact with recesses along the axial direction of the plunger, such that rotation of the gear results in axial movement of the plunger 8 through the main housing. As illustrated schematically in FIG. 2, a cap 11 mounted on the end of the plunger 8 acts on a "bung" 12 of the cartridge 13, driving medicament 14 from the cartridge, through an attached needle, as the plunger moves in the direction of arrow A.

When a dose has been administered, the cap 11 remains in contact with the bung 12 after driving it forwards. This can lead to leakage of the drug, since the bung is compressed by the action of the cap during the driving stroke, and will tend to expand to its original shape once the stroke is complete. This expansion can force liquid from the cartridge. In addition, the movement of the dose knob 3 when the dose is being set can cause vibrations, and these vibrations may be transmitted down the plunger 8 to the cap 11 and thus the bung 12, again forcing liquid from the capsule.

SUMMARY

It would therefore be desirable to provide an injection device adapted to prevent undesired leakage.

In accordance with one aspect of the present invention there is provided an injection device comprising a main housing, a plunger, a drive gear and a release trigger. The plunger comprises a leadscrew and a cap attached to the leadscrew such that, in use, the cap engages a bung of a cartridge containing medicament. The drive gear is located within the housing and engages with said leadscrew such that rotation of the drive gear drives the plunger axially through the housing towards the bung. The release trigger comprises a locking ring having generally axially extending teeth for engaging with corresponding teeth on the drive gear, the release trigger being generally axially movable between an engaged position in which the teeth are engaged so as to prevent rotation of the drive gear relative to the housing, and a disengaged position in which the teeth are disengaged so as to enable rotation of the drive gear. Movement of the release trigger between the disengaged position and the engaged position causes counter-rotation of the drive gear so as to retract the plunger away from the bung.

The release trigger may be located in a slot in the main housing, the slot including an axially extending section for guiding the trigger to the disengaged position, and a dogleg section corresponding to the engaged position of the trigger, the dogleg section extending in a direction including a circumferential component so that, as the release trigger moves through the dogleg section, it causes rotation of the drive gear.

The teeth of the locking ring may be bevelled at an end facing the drive gear such that, as the trigger moves from the disengaged position to the engaged position, they provide a rotation force on the teeth of the drive gear so as to cause the drive gear to counter-rotate. The teeth of the drive gear may have a corresponding bevel at an end facing the locking ring so as to react against the bevelled faces of the locking ring teeth. The counter-rotation may be one notch.

The teeth of the locking ring and teeth of the drive gear may have a screw pitch so that axial movement of the trigger between the disengaged position and the engaged position causes counter-rotation of the drive gear.

The drive gear may be configured to engage with a screw thread on the leadscrew on the plunger such that rotation of the drive gear around the leadscrew drives the plunger axially through the housing when the leadscrew is locked against rotation with respect to the housing.

In an alternative embodiment, the device may further comprise a static gear configured to engage with a screw thread on the leadscrew. In this embodiment the plunger is rotationally fixed relative to the drive gear such that rotation of the drive gear causes rotation of the leadscrew resulting in axial movement of the plunger relative to the static gear when the static gear is locked against rotation with respect to the housing. In this embodiment the cap may be rotatable relative to the leadscrew.

The invention also provides a method of operating the injection device described above. The method includes locating the release trigger in the engaged position so as to prevent rotation of the drive gear, storing rotational potential energy between the housing and the drive gear, moving the release trigger to the disengaged position, rotating the drive gear by release of the potential energy so as to drive the plunger axially towards the bung, returning the release trigger to the engaged position, and counter-rotating the drive gear so as to retract the plunger away from the bung

BRIEF DESCRIPTION OF THE DRAWINGS

Some preferred embodiments of the invention will now be described by way of example only and with reference to the accompanying drawings, in which:

FIG. 1 shows a horizontal cross-section through a prior art injector pen and a detail of the same horizontal cross-section;

FIG. 2 is a perspective view of a plunger of the device of FIG. 1, interacting with a medicament containing cartridge;

FIG. 3A is a perspective exploded view of an injector pen;

FIG. 3D is a detailed view of the drive gear and sliding trigger of FIGS. 3B and 3C in combination;

FIG. 5A is a perspective view of an alternative injector pen;

FIG. 5B is a top view of the housing of the injector pen of FIG. 5A; and

DETAILED DESCRIPTION

Figure 3C:
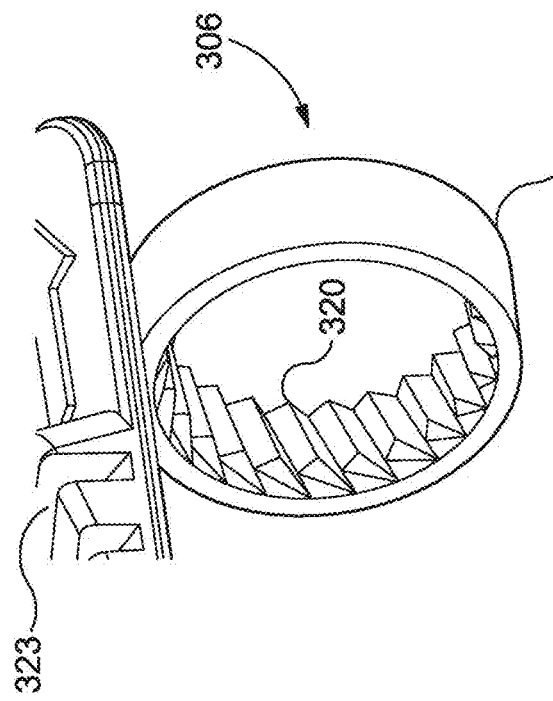
FIG. 3C is a detailed view of a sliding trigger used in the injector pen of FIG. 3A.
Figure 3B:
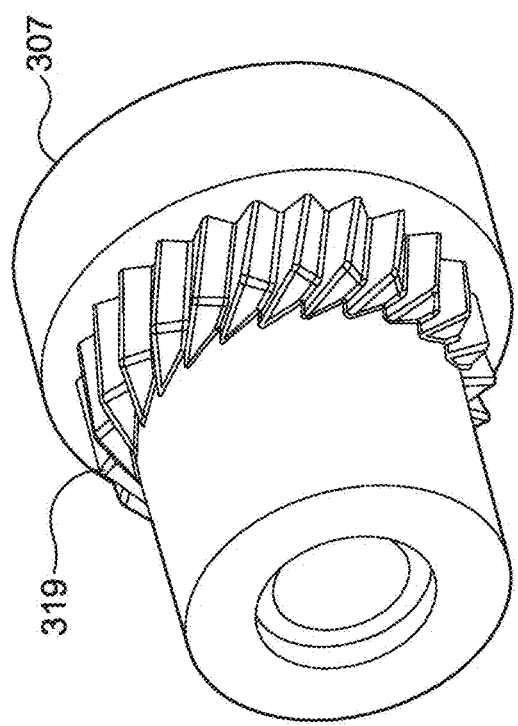
FIG. 3B is a detailed view of a portion of a drive gear used in the injector pen of FIG. 3A.

An injection device 300 similar to that shown in FIG. 1 is illustrated in exploded form in FIG. 3A. Features common to the device of FIG. 1 and the improved device are identified with like reference numerals. A dose knob 3 is provided at a proximal end of the device and which is rotatable with respect to the main housing 4. Rotation of the knob causes rotation of a drive sleeve 316, which may be a drive shaft, which stores energy in a torsion spring (not shown in FIG. 3). The drive sleeve 316 includes an annular ring 317 projecting at its distal end having at least one sprung tooth 318 protruding therefrom. The sprung tooth 318 cooperates with ratchet teeth (not shown) formed on an internal surface of a drive gear 307, and allows rotation of the drive sleeve 316 relative to the drive gear 307 in one direction only in a series of "clicks". The dose can thus be wound up in that direction, and the drive sleeve is prevented from unwinding by the ratchet teeth. The drive gear itself is prevented from unwinding by external teeth 319 which cooperate with internal teeth 320 of a locking ring 321 of the sliding trigger 306. The drive gear 307 and sliding trigger 306 are shown in more detail in FIGS. 3B, 3C and 3D.

The sliding trigger is coupled to the main housing 4 via a generally axial slot 322 such that a button 323 is located outside the housing 4 and the locking ring 321 is located inside the housing. The trigger 306 can therefore be moved axially but not circumferentially. Axial movement of the sliding trigger 306 disengages the teeth 320 of the locking ring 321 from the teeth 319 of the drive gear 307, thus allowing the drive gear 307 and drive shaft 316 to be rotated by unwinding of the torsion spring. The drive gear 307 is coupled to a plunger 8 via a quick pitch screw thread. During firing, the plunger 8 is prevented from rotating by splines 10 interacting with recesses 324 along the axial direction of the plunger, such that rotation of the drive gear 307 results in axial movement of the plunger through the main housing 4.

Rotation continues until an externally protruding latch 325 behind the annular ring 318 on the drive sleeve contacts a corresponding stop in a collar 326 fixed relative to the main housing 4. The sliding trigger 306 is then retracted again so that the internal teeth 320 of the locking ring 321 re-engage with the teeth 319 of the drive gear 307. An additional spring (not shown) may be provided to ensure that the trigger is retracted after use.

In order to prevent leakage, the cap 11 should be withdrawn a short distance from the bung once the dose has been dispensed. This can be achieved by counter-rotating the drive gear 307 after the plunger 8 has been driven the required distance, to bring the plunger back slightly.

This is achieved in the arrangement of FIG. 3A by the fact that the inner teeth 320 of the locking ring 321 do not extend purely axially, but have a screw pitch and therefore act as a thread. The outer teeth 319 on the drive gear 307 have a corresponding pitch so that the drive gear 307 is rotated slightly by axial movement of the sliding trigger 306. The direction of the thread is such that the forward movement of the trigger 306 rotates the drive gear 307 in the same direction as that caused by unwinding of the torsion spring.

When the user wishes to administer a dose, once the dose knob has been rotated to tension the torsion spring, the sliding trigger 306 is moved forwards (against the force of the additional spring, if present). The forward motion of the sliding trigger causes rotation of the drive gear 307, which intern causes the plunger 8 to be extended slightly. This short extension of the plunger 8 brings the cap 11 into contact with the bung. Further forward movement of the slider disengages the teeth 321 of the sliding trigger from those of the drive gear 307 once the cap is in contact with the bung, at which point the gear is rotated by the torsion spring so as to extend the plunger 8 and dispense the dose, in the same manner as the device of FIGS. 1 and 2.

Once the latch 325 has contacted the stop on the collar 326, the sliding trigger 306 is returned (by the additional spring, if present) along the axial slot 322 until the teeth (threads) 320 of the locking ring 321 engage those of the drive gear 307. Once the threads are engaged, further axial retraction of the sliding trigger 307 results in counter-rotation of the drive gear 307, which in turn retracts the plunger a short distance, thus lifting the cap 11 away from the bung. When the next dose is administered the first part of the slider movement again causes forward rotation of the drive gear 307 so as to extend the plunger 8 so that the cap 11 contacts the bung.

Figure 4A:
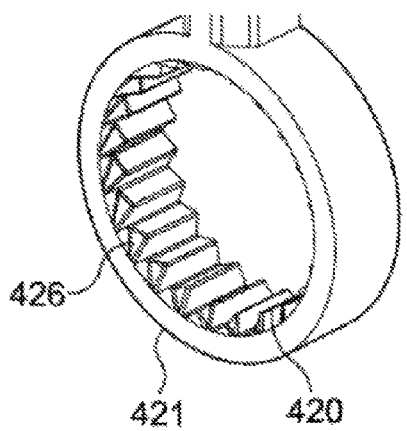
FIG. 4A is a perspective view of a locking ring.
Figure 4B:
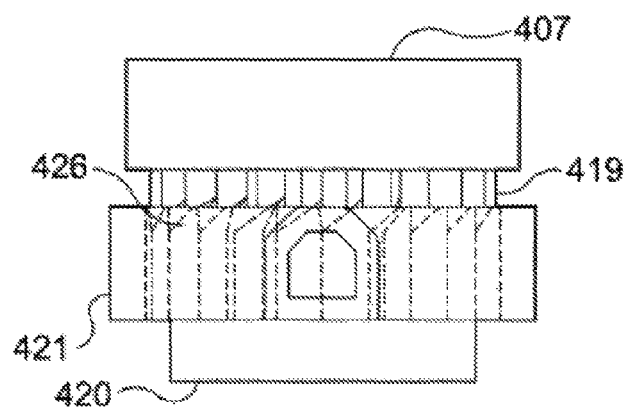
FIG. 4B is a perspective view of the locking ring of FIG. 4A engaged with a drive gear.

An alternative approach which achieves a similar effect is illustrated in FIG. 4B, which shows an alternative locking ring 421 and drive gear 407, which may be used in place of the locking ring 321 and drive gear 307 shown in FIG. 3A. The locking ring in isolation is shown in FIG. 4A. In this approach, the teeth 419, 420, of the drive gear 407 and locking ring 421 extend axially, but each tooth 420 of the locking ring 421 has a bevelled rear face 426. A corresponding front face of each tooth 419 of the drive gear is also bevelled. This means that, when the sliding trigger 406 is pushed forwards to initiate dispensing of the dose, no rotation is applied to the drive gear 407, and the plunger does not move axially until the teeth 419, 420 disengage. However, when the sliding trigger is retracted, the bevelled faces 426 of the teeth on the locking ring 421 contact the bevelled faces of the teeth 419 of the drive gear 407 and cause it to counter-rotate as the teeth re-engage, thus retracting the plunger 8 so that the cap 11 disengages from the bung. The counter-rotation may be one notch (i.e. one tooth of the drive gear).

A further alternative approach is illustrated in FIGS. 5A and 5B. FIG. 5A shows an exploded view of a device 500 similar to the device 300 shown in FIG. 3. The device differs from that of FIG. 3 in that the slot 522 in the main housing 504, along which the sliding trigger passes, is not purely axial but includes a dogleg section. The housing 504 is shown in more detail FIG. 5B, where it can be seen that the generally axial slot includes a front axial section 527 extending axially, a dogleg section 528 including a circumferential component, and a rear axial section 529. A further difference from the device of FIG. 3 is that the teeth 519, 520, on the drive gear 7 and locking ring 521 respectively, extend generally axially in the same way as on the device of FIG. 1.

When the device is at rest the sliding trigger 506 is held by a spring (not shown) at the rear end of the rear axial section of the slot such the teeth 520 of the locking ring engage the teeth 519 of the drive gear. When the user wishes to administer a dose, the sliding trigger 506 is moved forwards against the pressure of the spring. While the teeth are still engaged with the drive gear the sliding trigger moves along the dogleg section 528, and this motion includes a circumferential component. This movement results in a small rotation of the drive gear 507, resulting in a short extension of the plunger 8. This short extension of the plunger 8 brings the cap 11 into contact with the bung. Further forward movement of the sliding trigger 506 is along the front axial section 527 and this disengages the teeth 520 from those of the drive gear once the cap is in contact with the bung, at which point the gear is rotated by the torsion spring 5 so as to extend the plunger as before.

Once the drug dispensation is complete, the sliding trigger 506 is returned by the spring along the front axial section 527 of the slot 522 until the teeth 520 of the locking ring 521 engage those 519 of the drive gear 507. The sliding trigger 506 then continues to move along the dogleg section 528, so that the movement includes a circumferential component which counter-rotates the drive gear 507 and retracts the plunger a short distance, thus lifting the cap 11 away from the bung. When the next dose is administered the first part of the sliding trigger movement again includes a circumferential component so as to rotate the drive gear and extend the plunger 8 so that the cap 11 contacts the bung.

In each of these approaches it will be appreciated that, during dispensation, the first movement is a small rotation of the drive gear to bring the cap of the plunger into contact with the bung. The next movement is the release of the drive gear from the rotational constraint placed on it by the slider, at which stage it is rotated by the torsion spring (in the same direction as the initial small movement). Then as the slider is retracted there is a small counter-rotation of the drive gear which retracts the cap of the plunger away from contact with the bung.

As noted above, in the prior art arrangement of FIGS. 1 and 2, when a dose is being administered, rotation of the drive gear is stopped when a latch on the drive shaft encounters a stop fixed relative to the main housing. In the prior art configuration, when the slider is retracted the latch remains in contact with the stop, and this assists in holding the tension of the spring.

When the drive gear is counter-rotated slightly as the slider is retracted, this lifts the latch away from the stop. The torsion spring tension is therefore now held by the interaction between the ratchet teeth of the drive gear and the drive shaft. This means that, as the knob 3 is rotated to set the dose, there is no play in the initial movement. This reduces the manufacturing tolerances required in the manufacture of the drive shaft and drive gear.

It will be appreciated that the three approaches described above may be combined: for example the pitched teeth shown in FIGS. 3A to 3D may have bevelled ends, and may be used in conjunction with a doglegged slot.

It will also be appreciated that variations from the embodiments described above may fall within the scope of the invention.

Figure 6:
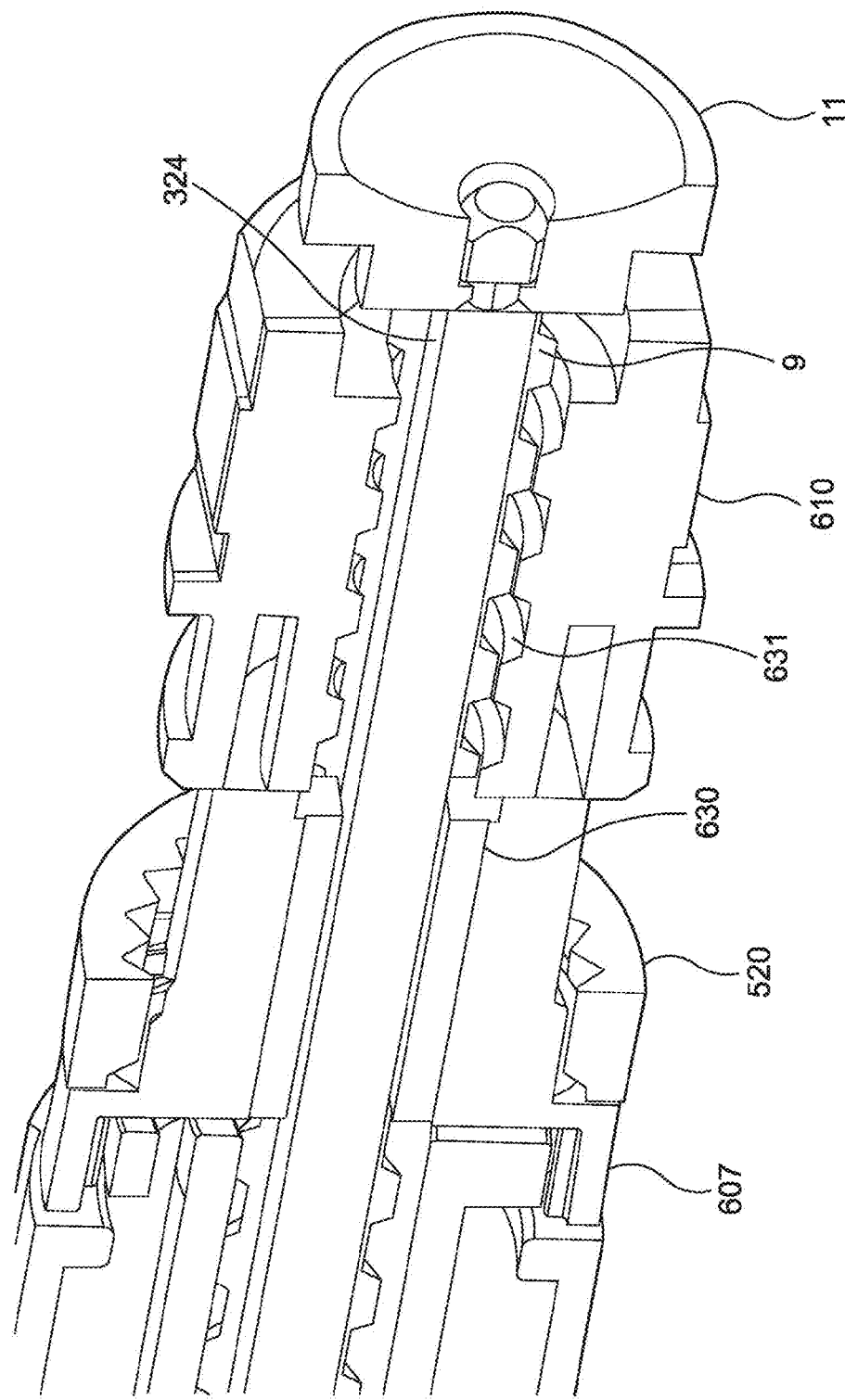
FIG. 6 is a schematic view of parts of an alternative injector pen.

For example, in the devices described above, the drive gear includes an internal thread which engages with the screw thread on the leadscrew of the plunger so as to drive the plunger axially when it is locked against rotation relative to the housing. However, in another arrangement (illustrated in FIG. 6) the plunger 8 may be locked rotationally relative to the drive gear 607, for example by the use of splines 630 which interact the recesses 324 in the plunger, so that rotation of the drive gear causes rotation of the plunger. A static gear, for example the rewind knob 610, may include an internal thread 631 so that rotation of the plunger causes axial movement relative to the rewind knob. The rewind knob 610 is lockable relative to the housing 4 when the cartridge housing 2 is attached to the main housing 4. This may be achieved by use of a locking bar (not shown). If this arrangement is used the cap 11 needs to be rotatable relative to the leadscrew 9 so that it does not rotate when in contact with the bung.

The invention claimed is:

1. An injection device comprising:
   a main housing;
   a plunger comprising a leadscrew and a cap attached to the leadscrew such that, in use, the cap engages a bung of a cartridge containing medicament;
   a drive gear within the housing and engaging with a said leadscrew such that rotation of the drive gear drives the plunger axially through the housing towards the bung; and
   a release trigger comprising a locking ring having generally axially extending teeth for engaging with corresponding teeth on the drive gear, the release trigger being generally axially movable between an engaged position in which the generally axially extending teeth of the locking ring and the corresponding teeth on the drive gear are engaged so as to prevent rotation of the drive gear relative to the housing, and a disengaged position in which the generally axially extending teeth of the locking ring and the corresponding teeth on the drive gear are disengaged so as to enable rotation of the drive gear;
   wherein the teeth of the locking ring and teeth of the drive gear have a screw pitch so that axial movement of the trigger between the disengaged position and the engaged position causes counter-rotation of the drive gear so as to retract the plunger away from the bung.

2. The injection device of claim 1, wherein the drive gear is configured to engage with a screw thread on the leadscrew on the plunger such that rotation of the drive gear around the leadscrew drives the plunger axially through the housing when the leadscrew is locked against rotation with respect to the housing.

3. The injection device of claim 1, further comprising a static gear configured to engage with a screw thread on the leadscrew, wherein the plunger is rotationally fixed relative to the drive gear such that rotation of the drive gear causes rotation of the leadscrew resulting in axial movement of the plunger relative to the static gear when the static gear is locked against rotation with respect to the housing.

4. A method of operating the injection device of claim 1, comprising:
   locating the release trigger in the engaged position so as to prevent rotation of the drive gear;
   storing rotational potential energy between the housing and the drive gear;
   moving the release trigger to the disengaged position;
   rotating the drive gear by release of the potential energy so as to drive the plunger axially towards the bung;
   returning the release trigger to the engaged position; and
   counter-rotating the drive gear so as to retract the plunger away from the bung.

5. The injection device of claim 1, wherein the drive gear is configured to engage with a screw thread on the leadscrew on the plunger such that rotation of the drive gear around the leadscrew drives the plunger axially through the housing when the leadscrew is locked against rotation with respect to the housing.

<div style="text-align:center">* * * * *</div>